US010932757B2

(12) United States Patent
Yang et al.

(10) Patent No.: US 10,932,757 B2
(45) Date of Patent: Mar. 2, 2021

(54) ULTRASONIC DIAGNOSIS APPARATUS AND POWER SUPPLY DEVICE

(71) Applicant: General Electric Company, Schenectady, NY (US)

(72) Inventors: Yalan Yang, Wuxi (CN); Hangjun Li, Wuxi (CN); Youqiu Liu, Wuxi (CN)

(73) Assignee: General Electric Company, Schenectady, NY (US)

( * ) Notice: Subject to any disclaimer, the term of this patent is extended or adjusted under 35 U.S.C. 154(b) by 756 days.

(21) Appl. No.: 15/581,478

(22) Filed: Apr. 28, 2017

(65) Prior Publication Data

US 2017/0311931 A1    Nov. 2, 2017

(30) Foreign Application Priority Data

Apr. 28, 2016 (CN) .......................... 201610274178.4

(51) Int. Cl.
*A61B 8/00* (2006.01)
*G01S 7/52* (2006.01)
*G01S 15/02* (2006.01)

(52) U.S. Cl.
CPC .............. *A61B 8/56* (2013.01); *A61B 8/4405* (2013.01); *G01S 7/52079* (2013.01); *G01S 7/52096* (2013.01); *G01S 15/02* (2013.01)

(58) Field of Classification Search
CPC ..... A61B 8/56; A61B 8/4405; G01S 7/52096; G01S 7/52079; G01S 15/02; Y02B 70/30; Y04S 20/20; H02J 9/02; H02J 9/061
See application file for complete search history.

(56) References Cited

U.S. PATENT DOCUMENTS

2009/0276637 A1* 11/2009 Coonan ................. H02J 7/0021
                                                                  713/300
2013/0076137 A1*  3/2013 Murtha ................. H02J 7/0068
                                                                  307/48

FOREIGN PATENT DOCUMENTS

KR          20120116321 A  * 10/2012  ........... A61B 8/4405

* cited by examiner

*Primary Examiner* — Daniel J Cavallari

(57) ABSTRACT

The present invention relates to an ultrasonic diagnosis apparatus and a power supply device. The ultrasonic diagnosis apparatus comprises: an ultrasonic host including a pluggable main battery pack; a backup power supply device including a plurality of pluggable backup battery packs, for powering the ultrasonic host; and a trolley for carrying the ultrasonic host and the backup power supply device; wherein a specification of each of the plurality of backup battery packs is identical to that of the main battery pack.

17 Claims, 4 Drawing Sheets

ULTRASONIC DIAGNOSIS APPARATUS AND POWER SUPPLY DEVICE

CROSS-REFERENCE TO RELATED APPLICATION

This patent application claims foreign priority benefits under 35 U.S.C. § 119 to Chinese Patent Application No. 201610274178.4, filed Apr. 28, 2016, which is hereby incorporated by reference in their entireties.

FIELD OF THE INVENTION

The present invention relates to the field of ultrasonic technology, particularly to an ultrasonic diagnosis apparatus and a power supply device.

BACKGROUND OF THE INVENTION

The existing movable ultrasonic diagnosis apparatus may usually include an ultrasonic host and a trolley. The ultrasonic host is usually designed with a smaller size, a lighter weight, for example, its outline style may be similar to a laptop. Thus, when the ultrasonic host needs to be pushed to a place where it is needed, the ultrasonic host may be placed on the trolley. The trolley may lift the ultrasonic host up and down to adapt to different application scenes. Furthermore, the trolley is also provided with wires, circuits and the like that may be connected to an external alternating current for powering the ultrasonic host.

In some places where the external alternating current cannot be used, a battery within the ultrasonic host needs to be used. A capacity of the battery within the ultrasonic host is smaller because it is limited by a volume of the ultrasonic host. However, one ultrasonic examination usually needs to last for a certain time. Hence, the trolley may be configured with a chargeable backup battery. When there is no external alternating current, the ultrasonic host is powered with this battery.

However, in order to make the capacity of the above backup battery as large as possible, a battery pack and its accompanying charge and discharge circuit are usually designed for the backup battery individually in the prior art, in which a size of this battery pack is totally different from that of the battery pack in a chargeable battery built in the ultrasonic host. This results in a problem that, when this entire set of ultrasonic diagnosis apparatus is under design/development and production/manufacture, two different kinds of battery packs need to be designed, purchased and manufactured, which elongates the period of designing a product and also increases the cost of developing and manufacturing the product. Furthermore, a user of the ultrasonic diagnosis apparatus cannot maintain and replace the battery in the ultrasonic diagnosis apparatus by himself, either.

BRIEF DESCRIPTION OF THE INVENTION

One embodiment of the present invention provides an ultrasonic diagnosis apparatus, comprising: an ultrasonic host including a pluggable main battery pack; a backup power supply device including a plurality of pluggable backup battery packs, for powering the ultrasonic host; and a trolley for carrying the ultrasonic host and the backup power supply device; wherein a specification of each of the plurality of backup battery packs is identical to that of the main battery pack.

Another embodiment of the present invention provides a power supply device, comprising: a plurality of pluggable backup battery packs, each of which has a specification identical to that of a pluggable main battery pack in a powered object.

BRIEF DESCRIPTION OF THE DRAWINGS

The present invention can be understood better in light of the description of embodiments of the present invention with reference to the accompanying drawings, in which.

DETAILED DESCRIPTION OF THE INVENTION

Hereafter, a detailed description will be given for preferred embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art relating to the contents disclosed in the present invention, which should not be regarded as insufficient disclosure of the present invention.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present utility model do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

In order to make the purpose, the technical solutions and the advantages of the invention more apparent, the technical solutions of the present invention will be set forth clearly and fully in the following by combining with specific embodiments of the invention and the corresponding accompanying drawings. Obviously, the described embodiments are merely part—not all—of the embodiments in the present invention. In view of the embodiments in the present invention, other embodiments made by one of ordinary skilled in the art without inventive work all fall within the scope of protection of the invention.

Figure 1:
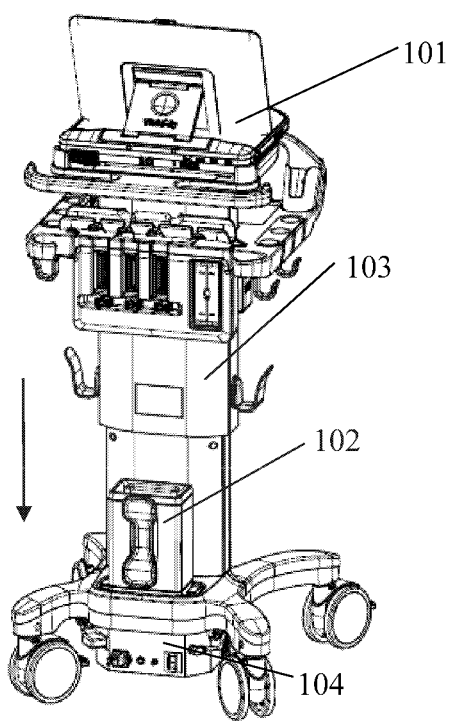
FIG. 1 illustrates a schematic diagram of one embodiment of an ultrasonic diagnosis apparatus of the present invention when a backup power supply device is plugged.

With reference to FIG. 1, FIG. 1 illustrates a schematic diagram of one embodiment of an ultrasonic diagnosis apparatus 100 of the present invention.

As shown in FIG. 1, the ultrasonic diagnosis apparatus 100 may include: an ultrasonic host 101, a backup power supply device 102, and a trolley 103.

The ultrasonic host 101 may be placed at a top of the trolley 103 and form electric connection with an electric connector on the trolley. The ultrasonic host 101 may include a pluggable main battery pack (not shown in the figure).

The trolley 103 may include a power box 104, one terminal of which may be connected with an alternating current of an external input and the other terminal of which may be connected with the backup power supply device 102. The trolley 103 may be used for carrying the ultrasonic host 101 and the backup power supply device 102.

Figure 2:
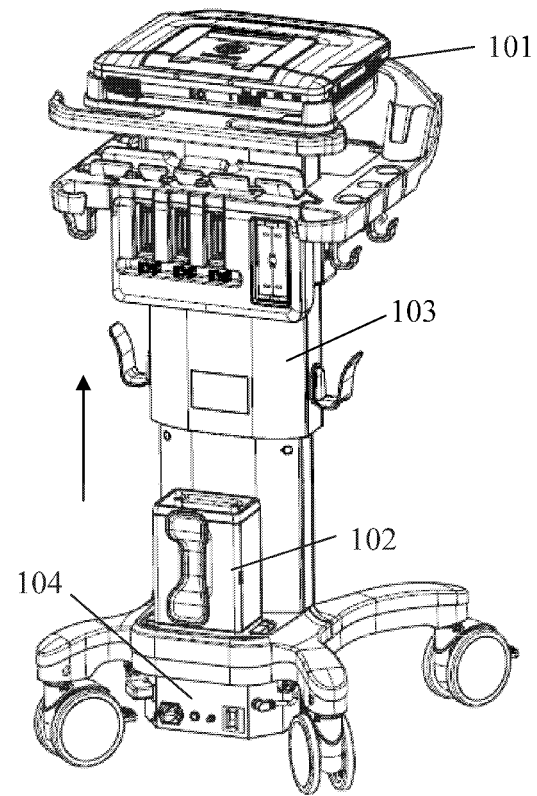
FIG. 2 illustrates a schematic diagram of one embodiment of an ultrasonic diagnosis apparatus of the present invention when a backup power supply device is unplugged.

The backup power supply device 102 may be plugged onto the power box 104 of the trolley 103 integrally along a direction indicated by an arrow in FIG. 1 so as to power the ultrasonic host 101 or to be charged. With reference to FIG. 2, the backup power supply device 102 may also be unloaded from the trolley integrally along a direction indicated by an arrow in FIG. 2.

Figure 5:
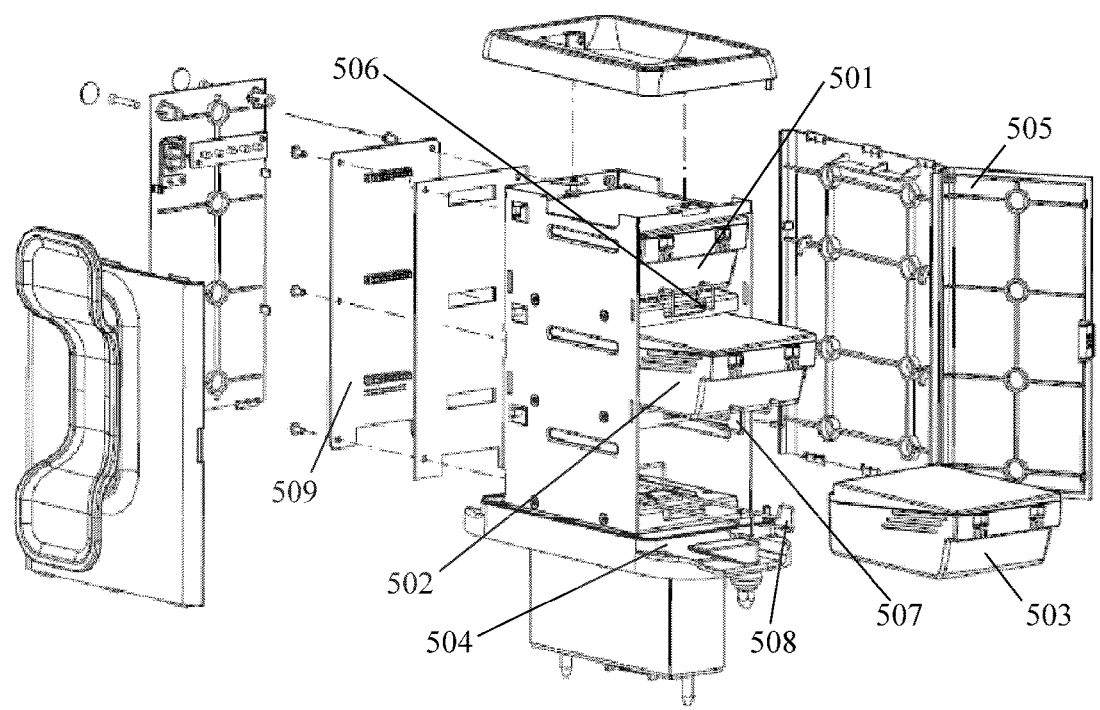
FIG. 5 illustrates a schematic diagram of one embodiment of an internal structure of a backup power supply device in an ultrasonic diagnosis apparatus of the present invention, i.e., a power supply device of the present invention.
Figure 6:
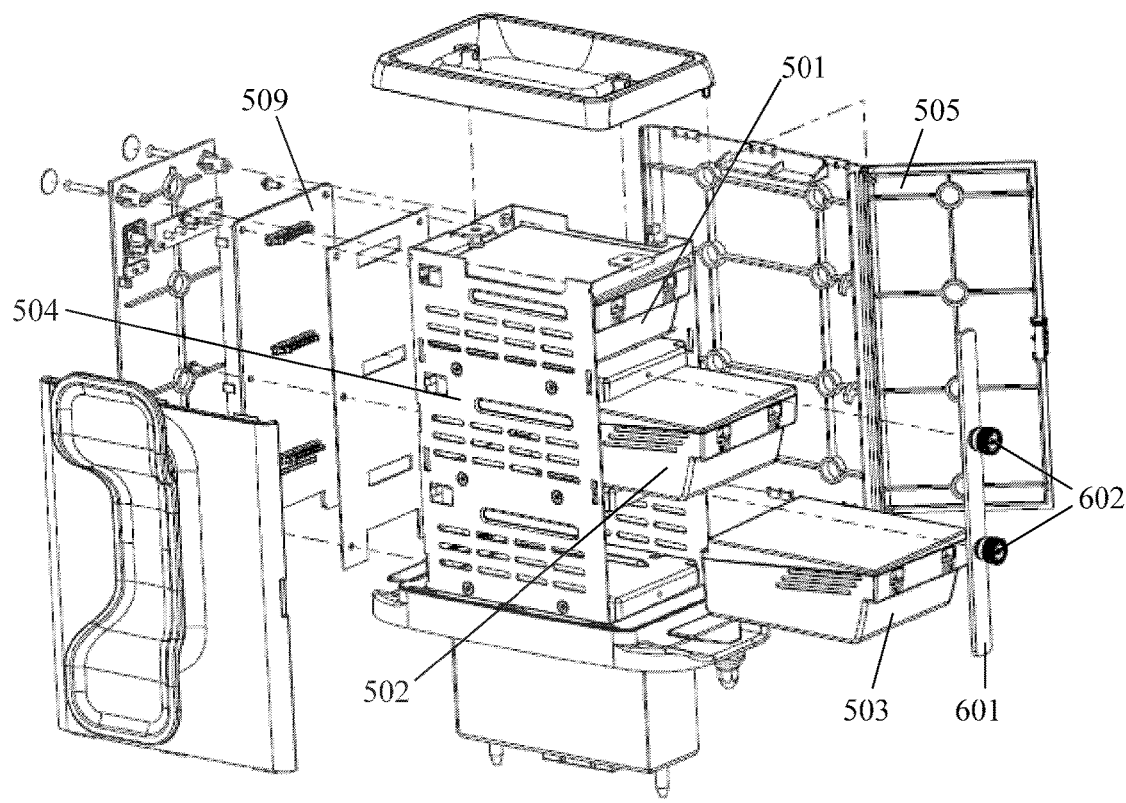
FIG. 6 illustrates a schematic diagram of another embodiment of an internal structure of a backup power supply device in an ultrasonic diagnosis apparatus of the present invention, i.e., a power supply device of the present invention.

In one embodiment of the present invention, the backup power supply device 102 may include a plurality of pluggable backup battery packs. With reference to FIG. 5 and FIG. 6, the backup power supply device 102 includes three pluggable backup battery packs 501, 502 and 503. All of these backup battery packs may be unplugged from the backup power supply device 102, and may also be plugged into the backup power supply device 102. A specification of each of the plurality of backup battery packs may be identical to that of the main battery pack in the ultrasonic host 101. In other words, a mechanical size of each backup battery pack is identical to that of the main battery pack, and an electrical specification of each backup battery pack is identical to that of the main battery pack.

In order to ensure that the backup power supply device 102 can be reliably plugged into the trolley 103 and form stable electric connection with the power box 104 on the trolley 103, the backup power supply device 102 and the trolley 103 may be designed in a mechanical aspect as below.

Figure 3:
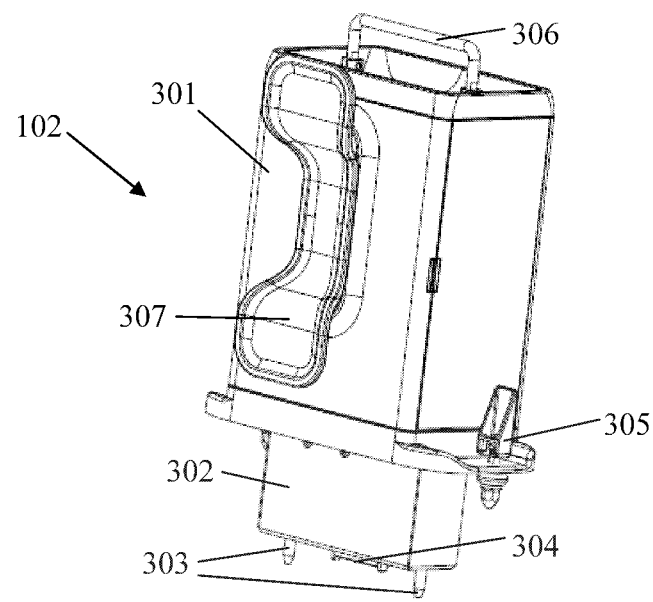
FIG. 3 illustrates a schematic diagram of one embodiment of an external structure of a backup power supply device in an ultrasonic diagnosis apparatus of the present invention, i.e., a power supply device of the present invention.

On the backup power supply device 102, with reference to FIG. 3, the backup power supply device 102 may include a housing 301, a guide block 302, a guide needle 303, an electric connector 304, and a locking member 305. The housing 301 may be used for enclosing the backup battery packs in the backup power supply device 102. The guide block 302 may be located at a bottom of the housing 301, for determining an approximate position of the backup power supply device 102 when the backup power supply device 102 is connected with the power box 104. The guide needle 303 may also be located at the bottom of the housing 301, for determining an exact position of the backup power supply device 102 when the backup power supply device 102 is connected with the power box 104. The electric connector 304 may be located at a lower part of the guide block 302, for being electrically connected with the power box 104. The locking member 305 may be located on the housing 301, for locking the backup power supply device 102 after the backup power supply device 102 has been connected with the power box 104.

In one embodiment of the present invention, the backup power supply device 102 may also include a handle 306, which may be located at the top of the housing 301 and may help a user to unplug the backup power supply device 102 from the power box 104 or to plug the backup power supply device 102 into the power box 104.

In one embodiment of the present invention, the backup power supply device 102 may include a hook 307, which may be located at one side on the housing 301 facing an operator, for receiving a power cord for providing an external alternating current for the power box 304.

Figure 4:
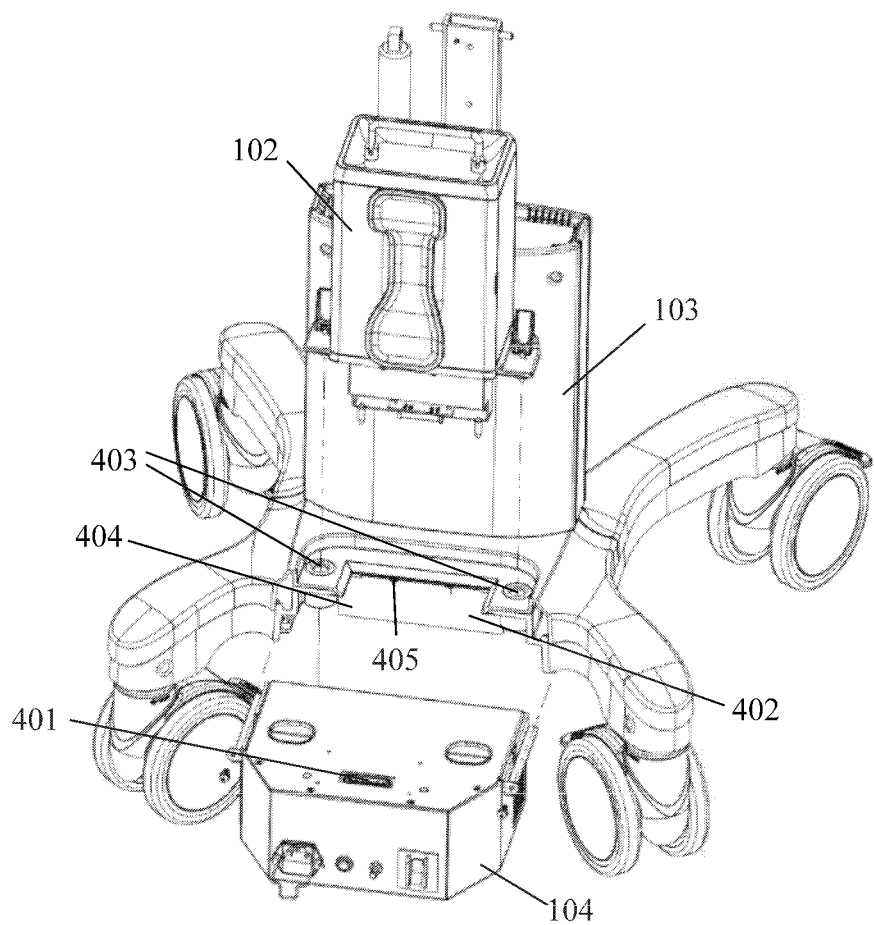
FIG. 4 illustrates a schematic diagram of one embodiment of a trolley in an ultrasonic diagnosis apparatus of the present invention.

Corresponding to the above design on the backup power supply device 102, with reference to FIG. 4, an electric socket 401, a guide hole 402 and a locking hole 403 may be included on the trolley 103 and the power box 104 on the trolley 103.

The electric socket 401 may have a size matching with that of the guide block 302 on the backup power supply device 102, for being connected with the electric connector 304. A size of the guide hole 402 may match with that of the guide needle 303 on the backup power supply device 102. When the guide needle 303 is inserted into the guide hole 402, the electric connector 304 can be appropriately connected with the electric socket 401. The locking hole 403 may lock the backup power supply device 102 onto the trolley 103 by way of coordination with the locking member 305 on the backup power supply device 102.

In one embodiment of the present invention, a dustproof member may also be provided above the electric socket 401. When the backup power supply device 102 is not plugged into the electric socket 401, the dustproof member may block the electric socket 401. In this way, a foreign object may be prevented from entering into the electric socket 401.

In one embodiment of the present invention, the dustproof member may further include: a blocking cover 404 and a torsional spring 405. The blocking cover 404 may block the electric socket 401. One end of the torsional spring 405 may be connected to the blocking cover 404, and the other end of the torsional spring 405 may be connected to a body of the power box. The blocking cover 404 may cover the electric socket 401 under an effect of resilience of the torsional spring 405 when the torsional spring 405 is not subject to a pressure of the guide block 302. When the guide block 302 on the backup power supply device 102 extrudes the blocking cover 404 during plugging of the backup power supply device 102 into the power box 104, the blocking cover 404 may be moved so as to expose the electric socket 401 in the power box 104.

FIG. 5 and FIG. 6 show embodiments of an internal structure of the backup power supply device 102. In one embodiment of the present invention, the backup power supply device 102 may include a bracket 504, a doorstop 505 and a fastening member. The bracket 504 may be located within the housing 301, which can support the backup battery packs. Each of the backup battery packs 501, 502 and 503 may be plugged into the bracket 504 or be unplugged from the bracket 504 independently. The doorstop 505 may block the bracket 504 and the backup battery packs 501, 502 and 503. When the backup battery packs are completely plugged into the bracket 504, the fastening member may fix the backup battery packs. In one embodiment of the present invention, with reference to FIG. 5, the fastening member may be a plurality of spring frames 506, 507 and 508, each of which is used for fastening one backup battery pack correspondingly. In another embodiment of the present invention, the fastening member may be a locking lever 601 with a locking nut 602.

When a backup battery pack in the backup power supply device 102 needs to be replaced or the main battery pack on the ultrasonic host needs to be charged, the backup power supply device 102 may be firstly unplugged from the trolley 103, and then the doorstop 505 is opened, the spring frame 506/507/508 is pulled or the locking nut 602 on the locking lever 601 is loosened, thus the backup battery pack needing to be replaced is unplugged from the bracket and a new backup battery pack or the main battery pack needing to be charged is plugged. Then, according to the actions in a sequence opposite to the above operations, the backup power supply device 102 may just be connected onto the trolley 103.

In order to perform charge and discharge management on the plurality of backup battery packs in the backup power supply device, the power box 304 on the trolley 103 and the backup power supply device 102 may be designed in an electrical aspect as below.

Figure 7:
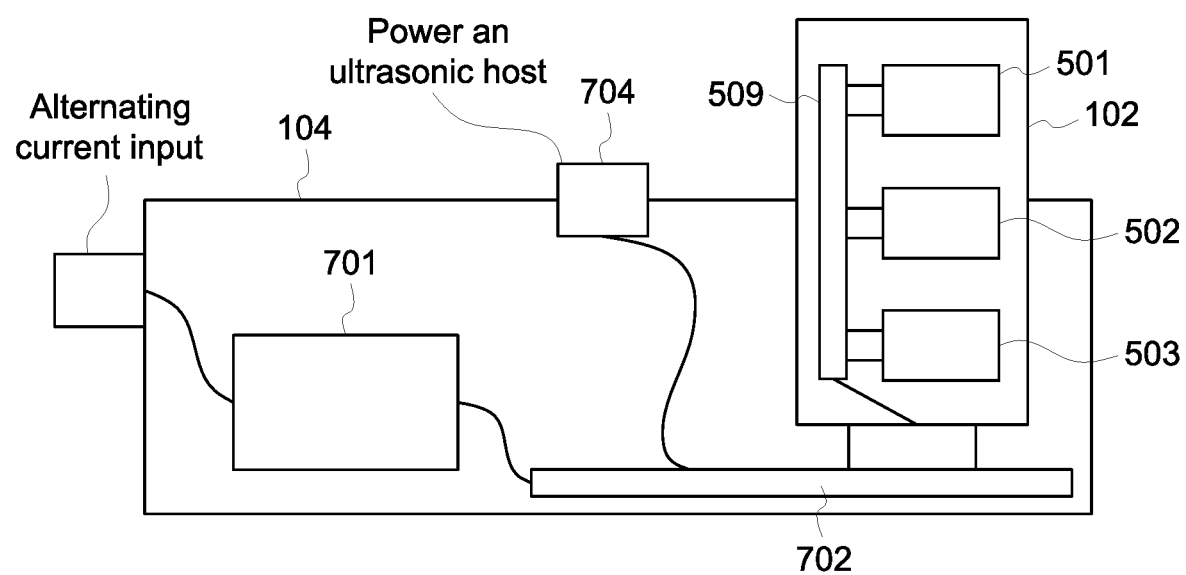
FIG. 7 illustrates a schematic diagram of one embodiment of electrical connection relationship between a trolley in an ultrasonic diagnosis apparatus and a backup power supply device of the present invention.

With reference to FIG. 7, in one embodiment of the present invention, the power box 304 may further include an AC-DC converter 701 and a power supply section module 702. The AC-DC converter 701 may convert an alternating current of an external input into a direct current. An input terminal of the power supply selection module 702 is connected with an output terminal of the AC-DC converter 701 and an output terminal of each of the plurality of backup battery packs 501, 502 and 503, for selecting a current source to power the ultrasonic host. When there is an output at the output terminal of the AC-DC converter 701, the power supply selection module 702 may select an output current of the AC-DC converter 701 to power the ultrasonic host. When there is no output at the output terminal of the AC-DC converter 701, the power supply selection module 702 may, according to a magnitude of an output voltage of each of the plurality of backup battery packs 501, 502 and 503, decide whether a corresponding backup battery pack is used for powering the ultrasonic host. For example, the power supply selection module 702 may select one or more backup battery packs with a maximum output voltage among the plurality of backup battery packs to power the ultrasonic host.

In one embodiment of the present invention, the power box 304 may also include a voltage regulation module with an input terminal connected with an output terminal of the power supply selection module 702. The voltage regulation module may keep an output voltage of the power supply selection module 702 stable. Especially when the remaining power of the backup battery packs is less and the output voltage is lower, the voltage regulation module may increase the voltage to the required voltage value.

In one embodiment of the present invention, the power box 304 may also include a voltage detection module 704, which may detect an output voltage of each of the plurality of backup battery packs 501, 502 and 503 and send it to the ultrasonic host. In this way, the user may see the current information of the remaining power of the individual backup battery packs on the ultrasonic host.

Corresponding to the above electrical design within the power box, in one embodiment of the present invention, a plurality of charging modules may be provided within the backup power supply device 102. An input terminal of each charging module may be connected with an output of the AC-DC converter 701 and the charging modules may charge each of the plurality of backup battery packs. In one embodiment of the present invention, the plurality of charging modules may be located on a circuit board 509 as shown in FIG. 5 and FIG. 6.

So far, the ultrasonic diagnosis apparatus according to the embodiments of the present invention has been described. The ultrasonic diagnosis apparatus according to the present invention is capable of both providing a backup power supply device with a large amount of power for the ultrasonic host and facilitating the user to replace the backup battery packs in the backup power supply device by himself. Moreover, the main battery pack within the ultrasonic host may also be exchanged with the backup battery packs in the backup power supply device. Thus the cost and period for designing, developing and manufacturing the product can be reduced.

The present invention also provides a power supply device. With reference to FIG. 5 and FIG. 6, the power supply device 102 may include a plurality of pluggable backup battery packs 501, 502 and 503, each of which has a specification identical to that of a pluggable main battery pack in a powered object.

In one embodiment of the present invention, the power supply device may include a plurality of charging modules, which may charge each of the plurality of pluggable backup battery packs with a direct current. The plurality of charging modules may be located on the circuit board 509.

As shown in FIG. 5 and FIG. 6, in one embodiment of the present invention, the power supply device 102 may also include: a bracket 504, which supports each of the plurality of pluggable backup battery packs to be capable of being plugged into the power supply device 102 or unplugged from the power supply device 102 independently; a doorstop 505 for blocking the bracket and the pluggable backup battery packs; and a fastening member for fixing the pluggable backup battery packs when the pluggable backup battery packs are completely plugged into the bracket.

With reference to FIG. 3, the power supply device 102 may also include: a housing 301 for enclosing the backup battery packs; a guide block 302, which is located at the bottom of the housing 301, for determining an approximate position of the power supply device 102 when the power supply device 102 is connected with an external electric interface; a guide needle 303, which is located at the bottom of the housing 301, for determining an exact position of the power supply device 102 when the power supply device 102 is connected with the external electric interface; an electric connector 304, which is located at the lower part of the guide block, for being connected with the external electric interface; and a locking member 305, which is located on the housing 301, for locking the power supply device 102 after the power supply device 102 has been connected with the external electric interface.

So far, the power supply device according to the embodiments of the present invention has been described. The device according to the present invention can facilitate the user to replace the backup battery packs in the device by himself. Moreover, the main battery pack within the powered object may also be exchanged with the backup battery packs in the backup power supply device. Thus the cost and period for designing, developing and manufacturing the product can be reduced.

The above descriptions are merely embodiments of the invention and are not intended to restrict the scope of the invention. All kinds of variations and modifications could be made to the present invention to those skilled in the art. Any modifications, alternatives and improvements made within the spirit and principles of the present invention shall fall within the scope of the appended claims.

What is claimed is:

1. An ultrasonic diagnosis apparatus, comprising:
   an ultrasonic host including a pluggable main battery pack;
   a backup power supply device including a plurality of pluggable backup battery packs; and
   a trolley for carrying said ultrasonic host and said backup power supply device;
   wherein a specification of each of said plurality of backup battery packs is identical to that of said main battery pack
   wherein the ultrasonic host is configured to be powered by the backup power supply device when the ultrasonic host is placed on the trolley and in an electric connection with the backup power supply, and wherein the host is configured to be powered by the main battery pack when host is removed from the trolley and the electric connection with the backup power supply has been broken.

2. The ultrasonic diagnosis apparatus according to claim 1, wherein said trolley further comprises: a power box with one terminal connected with an alternating current of an external input and the other terminal connected with the backup power supply device.

3. The ultrasonic diagnosis apparatus of claim 2, wherein said power box further comprises an AC-DC converter for converting the alternating current of the external input into a direct current.

4. The ultrasonic diagnosis apparatus of claim 3, wherein the backup power supply device is configured to identify an output voltage of each of the plurality of backup battery packs and send the output voltage of each of the plurality of backup battery packs to the ultrasonic host.

5. The ultrasonic diagnosis apparatus of claim 2, wherein said backup power supply device comprises a guide structure for determining a position of said backup power supply device when the backup power supply device is connected with said power box.

6. The ultrasonic diagnosis apparatus of claim 5, further comprises a housing for enclosing said backup battery packs, and wherein the guide structure comprises at least one of a guide block, a guide needle, and a guide hole.

7. The ultrasonic diagnosis apparatus of claim 6, wherein the guide structure comprises the guide needle and the guide hole, wherein the guide hole has a size matching the guide needle, wherein an electric connector located at a lower part of said guide block can appropriately be connected with an electric socket located on the power box when said guide needle is inserted into said guide hole.

8. The ultrasonic diagnosis apparatus of claim 7, wherein the guide structure further comprises the guide block for determining an approximate position of said backup power supply device when the backup power supply device is connected with said power box, and wherein the guide needle is for determining an exact position of said backup power supply device when the backup power supply device is connected with said power box.

9. The ultrasonic diagnosis apparatus of claim 1, wherein each of the plurality of pluggable backup battery packs is configured to be unplugged from the backup power supply device and exchanged with the main battery pack in the ultrasonic host.

10. An ultrasonic diagnosis apparatus, comprising:
    an ultrasonic host including a pluggable main battery pack;
    a backup power supply device including a plurality of pluggable backup battery packs, for powering said ultrasonic host; and
    a trolley for carrying said ultrasonic host and said backup power supply device, wherein said trolley comprises a power box with one terminal connected with an alternating current of an external input and the other terminal connected with the backup power supply device;
    wherein a specification of each of said plurality of backup battery packs is identical to that of said main battery pack;
    wherein said backup power supply device further comprises:
      a housing for enclosing said backup battery packs;
      a guide block, which is located at a bottom of said housing, for determining an approximate position of said backup power supply device when the backup power supply device is connected with said power box;
      a guide needle, which is located at the bottom of said housing, for determining an exact position of said backup power supply device when the backup power supply device is connected with said power box;
      an electric connector, which is located at a lower part of said guide block, for being connected with said power box; and
      a locking member, which is located on said housing, for locking said backup power supply device after the backup power supply device has been connected with said power box.

11. The ultrasonic diagnosis apparatus according to claim 10, wherein said backup power supply device further comprises:
    a handle, which is located at a top of said housing, for unplugging said backup power supply device from said power box or plugging said backup power supply device into said power box; and
    a hook, which is located at one side on said housing facing an operator, for receiving a power cord for providing an external alternating current for said power box.

12. The ultrasonic diagnosis apparatus according to claim 10, wherein said power box further comprises:
    an electric socket having a size matching with that of said guide block, for being connected with said electric connector;
    a guide hole having a size matching with said guide needle, wherein said electric connector can appropriately be connected with said electric socket when said guide needle is inserted into said guide hole;

a locking hole used on said trolley, for locking said backup power supply device onto said trolley by way of coordination with said locking member; and a dustproof member, which is located above said electric socket, for blocking said electric socket when said backup power supply device is not plugged into said electric socket.

13. The ultrasonic diagnosis apparatus according to claim 12, wherein said dustproof member further comprises:

a blocking cover for blocking said electric socket;

a torsional spring with one end connected to said blocking cover and the other end connected to a body of said power box, wherein when the torsional spring is not subject to a pressure of said guide block, said blocking cover covers said electric socket under an effect of resilience of said torsional spring.

14. The ultrasonic diagnosis apparatus according to claim 10, wherein said backup power supply device further comprises:

a bracket, which is located within said housing, for supporting each of said plurality of backup battery packs to be capable of being plugged or unplugged independently;

a doorstop for blocking said bracket and said backup battery packs; and a fastening member for fixing the backup battery packs when the backup battery packs are completely plugged into said bracket.

15. The ultrasonic diagnosis apparatus according to claim 14, wherein said fastening member is a plurality of spring frames, each of which is used for fastening one backup battery pack.

16. The ultrasonic diagnosis apparatus according to claim 14, wherein said fastening member is a locking lever with a locking nut.

17. A power supply device, comprising:

a plurality of pluggable backup battery packs, each of which has a specification identical to that of a pluggable main battery pack in a powered object;

a housing for enclosing said backup battery packs;

a guide block, which is located at a bottom of said housing, for determining an approximate position of said power supply device when the power supply device is connected with an external electric interface;

a guide needle, which is located at the bottom of said housing, for determining an exact position of said power supply device when the power supply device is connected with the external electric interface;

an electric connector, which is located at a lower part of said guide block, for being connected with said external electric interface; and a locking member, which is located on said housing, for locking said power supply device after the power supply device has been connected with said external electric interface.

* * * * *